(12) United States Patent
Xu et al.

(10) Patent No.: US 9,469,593 B2
(45) Date of Patent: Oct. 18, 2016

(54) PROCESS FOR PREPARING CINACALCET HYDROCHLORIDE

(71) Applicants: Shanghai Jingxin Biomedical Co., Ltd., Shanghai (CN); Shangyu Jingxin Pharmaceutical Co., Ltd., Shangyu, Zhejiang (CN)

(72) Inventors: Miaohuan Xu, Shanghai (CN); Yue Huang, Shanghai (CN); Min Zhang, Shanghai (CN)

(73) Assignees: Shanghai Jingxin Biomedical Co., Ltd., Shanghai (CN); Shangyu Jingxin Pharmaceutical Co., Ltd., Shangyu, Zhejiang (CN)

( * ) Notice: Subject to any disclaimer, the term of this patent is extended or adjusted under 35 U.S.C. 154(b) by 41 days.

(21) Appl. No.: 14/556,026

(22) Filed: Nov. 28, 2014

(65) Prior Publication Data

US 2015/0080608 A1    Mar. 19, 2015

Related U.S. Application Data

(63) Continuation-in-part of application No. PCT/CN2013/000066, filed on Jan. 21, 2013.

(30) Foreign Application Priority Data

May 29, 2012    (CN) .......................... 2012 1 0170026

(51) Int. Cl.
| | | |
|---|---|---|
| C07C 209/02 | (2006.01) | |
| C07C 209/16 | (2006.01) | |
| C07C 209/08 | (2006.01) | |

(52) U.S. Cl.
CPC ........... *C07C 209/02* (2013.01); *C07C 209/08* (2013.01); *C07C 209/16* (2013.01)

(58) Field of Classification Search
None
See application file for complete search history.

(56) References Cited

U.S. PATENT DOCUMENTS

| | | |
|---|---|---|
| 6,211,244 B1 | 4/2001 | Van Wagenen et al. |
| 7,250,533 B2 | 7/2007 | Lifshitz-Liron et al. |
| 7,449,603 B2 | 11/2008 | Lifshitz-Liron et al. |
| 2008/0146845 A1 | 6/2008 | Gome et al. |

FOREIGN PATENT DOCUMENTS

| | | |
|---|---|---|
| CN | 101941911 A | 1/2011 |
| WO | WO 2006/127933 A1 | 11/2006 |
| WO | WO 2008/117299 A1 | 10/2008 |
| WO | WO 2010/004588 A2 | 1/2010 |
| WO | WO 2010/010359 A1 | 1/2010 |

OTHER PUBLICATIONS

L.A. Sorbera et al., Cinacalcet Hydrochloride, Drug of the Future (27), 9, 931 (2002).
G.B. Shinde et al., Industrial Application of the Forster Reaction: Novel One-Pot Synthesis of Cinacalcet Hydrochloride, a Calcimimetic Agent, Org. Process Res. Dev., 15(2), pp. 455-461 (2011).

*Primary Examiner* — Clinton Brooks
(74) *Attorney, Agent, or Firm* — Mei & Mark LLP; Manni Li

(57) ABSTRACT

Method for preparing cinacalcet hydrochloride having the steps of heating (R)-1-naphthyl ethylamine (Formula I) and 3-(trifluoromethyl)benzene (Formula II)

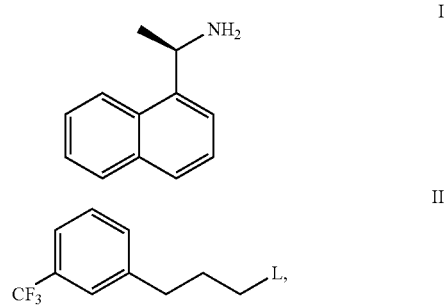

wherein L is a halogen atom, methanesulfonate group (OMs), p-Toluenesulfonate (OTs), or triflate (OTf), in an organic solvent in presence of an inorganic base, refluxing until 3-(trifluoromethyl)benzene is completely consumed, obtaining a reaction mixture containing cinacalcet, and after treatment, obtaining cinacalcet hydrochloride having a formula of

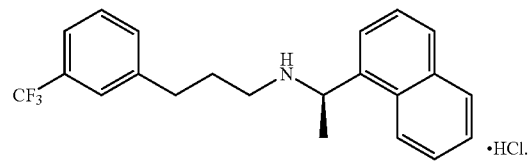

The post treatment separates (R)-1-naphthyl ethylamine hydrochloride and cinacalcet hydrochloride by adjusting pH value, extraction, and other simple operations, and the (R)-1-naphthyl ethylamine obtained is recycled for preparing the next batch of cinacalcet hydrochloride.

11 Claims, No Drawings

PROCESS FOR PREPARING CINACALCET HYDROCHLORIDE

CROSS-REFERENCE TO RELATED APPLICATIONS

The subject application is a continuation-in-part of PCT international application PCT/CN2013/000066 filed on Jan. 21, 2013, which in turn claims priority on Chinese patent applications CN 201210170026.1 filed on May 29, 2012. The contents and subject matter of the PCT and Chinese priority applications are incorporated herein by reference.

FIELD OF THE INVENTION

The subject application relates to a process for preparing drug substance, particularly, for preparing a calcimimetic agent, cinacalcet hydrochloride.

BACKGROUND OF THE INVENTION (R)—N-(1-(naphthalen-1-yl)ethyl)-3-(3-(trifluoromethyl)phenyl)propan-1-amine has the international non-proprietary name as cinacalcet [CAS number 226456-56-0] and chemical structure as follows:

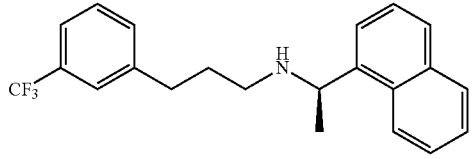 [SMILES: C[C@@H](NCCCc1cccc(C(F)(F)F)c1)c1cccc2ccccc12]

Cinacalcet is the free base of cinacalcet hydrochloride [CAS Number, 364782-34-3], and the chemical structure of cinacalcet hydrochloride is shown as follows:

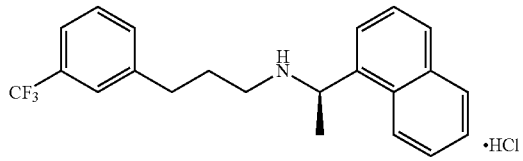 [SMILES: C[C@@H](NCCCc1cccc(C(F)(F)F)c1)c1cccc2ccccc12 ; Cl]

It is reported by NPS Pharma. Inc. that cinacalcet hydrochloride (the brand name is Sensipar) is a calcimimetic agent, which is a drug substance that can effectively treat the primary hyperparathyroidism (PHPT). Currently, it has been reported to have the following preparation methods for cinacalcet:

(1) Reductive Amination

U.S. Pat. No. 6,211,244 and Drugs of the future (27), 9, 931, 2002, disclose a process to prepare cinacalcet by reductive amination as illustrated below:

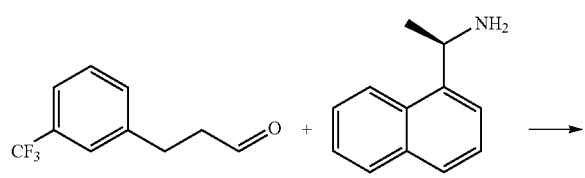

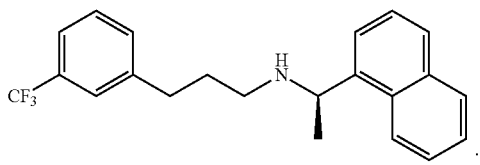

However, the method is unsuitable for industrial production due to the toxicity of the reductant sodium cyanoborohydride, the high cost and easy hydrolysis of tetraisopropyl titanate, and unavoidable over-reductive impurities produced in the post-production process, which results in difficult operation, tedious purification and low yield, etc. The over-reductive impurities are difficult to be avoided even by catalytic hydrogenation reduction using heavy metals palladium and platinum as catalysts.

(2) Amide Reduction

Alternatively, WO2007127445 and WO 2008117299 disclose the process as illustrated below:

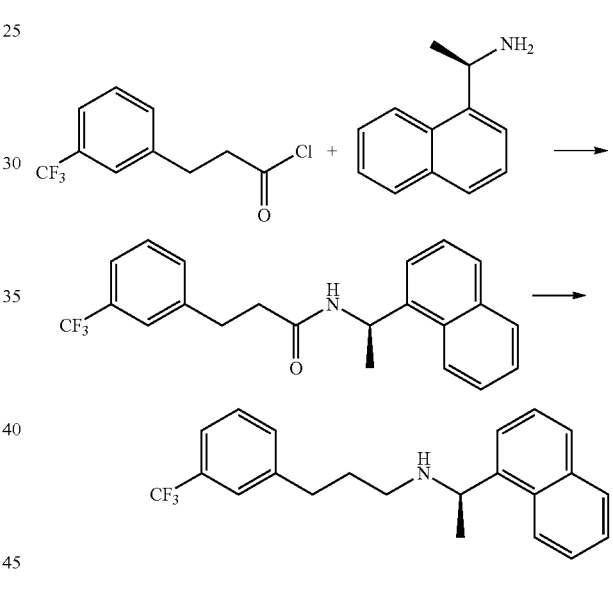

First, 3-trifluoromethylphenyl propionic acid is used to prepare acyl chloride; then, acyl chloride and (R)-1-naphthyl ethylamine are condensed to obtain amide; finally, carbonyl in amide is reduced to obtain cinacalcet. In the reduction of carbonyl, the reagents used, such as BF3, LiAlH4, or NaBH4/I2, NaBH4/AlCl3 bring difficulties in the operation and cause post treatment problems, so the method is not suitable for scale-up production. Additionally, the process is disfavored for industrial implementation due to the use of hazardous chemicals such as NaBH4/I2, NaBH4/AlCl3, protonic acid, as the large quantity of the chemicals will cause the difficulties of obtaining the high yield as claimed in the articles and too much trouble in work up and purification.

(3) Alkylation

A method of direct alkylation of mesylate (a compound of Formula II, L is methanesulfonate group (OMS)) is published in Chinese Patent No. CN101180261:

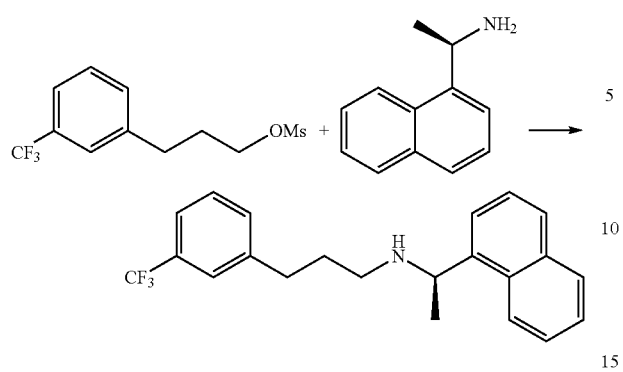

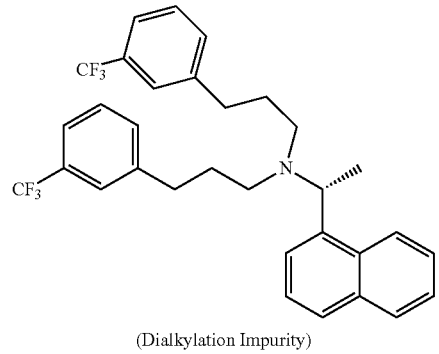

(Dialkylation Impurity)

In the process, residual (R)-1-(naphthalen-1-yl)ethan-1-amine is not effectively removed from the product because of its similar properties with cinacalcet, as both are alkaline substances. And (R)-1-naphthyl ethylamine is obtained by resolution or asymmetric synthesis, so the cost is high. In order to reduce the cost, the reported synthesis method by direct alkylation uses excessive amount of formula II compound to consume (R)-1-naphthyl ethylamine at maximum, and salify the product by adjusting pH. The unconsumed formula II compound and product could be separated due to the non-salification of excessive formula II compound. But the excessive amount of formula II compound may result in the large amount of dialkylation impurity (Formula IV Compound) present in the final product of alkylation (in the mixtures of end reaction, the content of dialkylation impurity may reach about 7%), while this impurity is an alkaline substance and hard to be separated from cinacalcet. In another aspect, the excessive amount of formula II compound results in the formation of large amount of impurity carbamic acid ester (Formula III Compound), which makes the post treatment of separation and purification more difficult, the yield decreases, and the impurity is difficult to be removed by simply adjusting pH or re-crystallization. See below for formulae II, III, and IV.

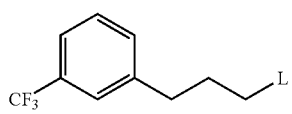

II

Where L is a halogen atom, methanesulfonate group (OMs), p-Toluenesulfonate (OTs), or triflate (OTf).

A Forster-Deker method which is improved from direct alkylation to avoid the by-products of dialkylation, is reported in Org. Process Res. Dev, 2011, 15 (2), P455-461, but due to the solubility problem of intermediate imine, big steric hindrance and little nucleophilicity, the yield may not reach expectation, and the increased steps and operations make the improvement of the method loss outweigh the gain. Similar problems are reported in WO2010004588, such as by the method first forms sulfamide, followed by alkylation and de-protection group, and in WO2010010359, first forms benzylamine, then alkylation and de-benzylation, etc. All these methods are difficult to be industrialized because of the prolongation of steps, difficult group protection and de-protection, abruptly increased environment protection pressure and costs.

SUMMARY OF THE INVENTION

The purpose of the present invention is to solve the deficiencies of the above methods, research and design a preparation method for cinacalcet hydrochloride, which is simple for operation and recovery of (R)-1-naphthyl ethylamine yet with high yield and low impurities.

The present invention provides a method for preparing cinacalcet hydrochloride having the following steps:

charging (R)-1-naphthyl ethylamine (Formula I Compound) and 3-(trifluoromethyl) benzene compound (Formula II Compound) at a ratio of (1.0-5.0):1, heating the mixture in an organic solvent in presence of an inorganic base, refluxing and reacting until formula II compound disappears, obtaining a cinacalcet-containing reaction mixture, and obtaining cinacalcet hydrochloride after acidification with hydrochloride and extraction from the reaction mixture.

III

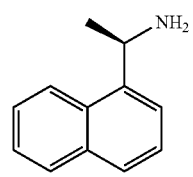

Formula I (Carbamic Acid Ester Impurity)

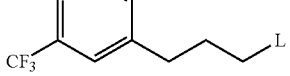

Formula II

In Formula II, L is a halogen atom, methanesulfonate group (OMs), p-Toluenesulfonate (OTs), or triflate (OTf).

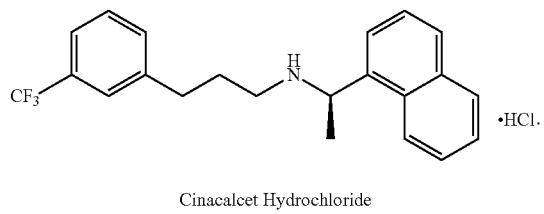 [SMILES: C[C@@H](NCCCc1cccc(C(F)(F)F)c1)c1cccc2ccccc12 ; Cl]

Cinacalcet Hydrochloride

In the method of the present invention, the molar ratio of (R)-1-naphthyl ethylamine (Formula I Compound) to Formula II Compound may be (1.0-3.0): 1, preferably, (1.0-2.0):1.

The molar ratio of the inorganic base and (R)-1-naphthyl ethylamine (Formula I Compound) is (1.0-2.0):1.

The inorganic base is potassium carbonate, sodium carbonate, sodium bicarbonate, potassium bicarbonate, potassium hydroxide, or sodium hydroxide.

Another purpose of the present invention is to provide a post treatment method for the above-mentioned mixture containing cinacalcet, including:

① Washing the cinacalcet mixture with water, separating and discarding the water phase, adding hydrochloric acid into the organic phase.

② Heating the mixture of the organic layer with the hydrochloric acid layer (40° C. –80° C.) until clear, separating the organic phase and the hydrochloric acid phase before cooling.

③ Allowing the organic layer as obtained in step ② cooled to 0° C.-30° C., crystallizing and filtering to obtain cinacalcet hydrochloride.

④ Adjusting pH value of the hydrochloric acid layer as obtained in step ② to 8-14 with an inorganic base, extracting with an organic solvent from one to five times, each time with a solvent 1 to 10 times the quantity of (R)-1-naphthyl ethylamine (W/V), combining the organic phases and discard solvents to recover the (R)-1-naphthyl ethylamine (Formula I Compound).

The molar ratio of hydrochloric acid used in post treatment step ① to raw material (R)-1-naphthyl ethylamine (Formula I Compound) is (1.0-5.0):1.

The inorganic base used in step ④ is potassium carbonate, sodium carbonate, potassium bicarbonate, sodium bicarbonate, potassium hydroxide, or sodium hydroxide. The organic solvent used in extraction is toluene, ethyl acetate, dichloromethane, methyl tert-butyl ether, pinacolone, or acetonitrile, and preferably, toluene, ethyl acetate, or dichloromethane.

In the present invention, the generation of the by-products of dialkylation (Formula IV Compound) is ultimately controlled by over charge of (R)-1-naphthyl ethylamine. It is surprising to find that, because of the over charge of (R)-1-naphthyl ethylamine, the content of the by-products of dialkylation (Formula IV Compound) and by-products of dialkylation (Formula IV Compound) are greatly decreased from more than 7% to not more than 1% in the final mixture of alkylation reaction. What's more, with the charge ratio, the content of the by-products of carbamate (Formula III Compound) is also decreased to below 0.1%. The present invention greatly simplifies the post treatment process and the impurity control method, and enables the impurity control easily to be carried out. Meanwhile, the solubility of excessive unconsumed (R)-1-naphthyl ethylamine hydrochloride and of cinacalcet hydrochloride in slightly heated organic solvents is apparently different. In the post treatment process, the (R)-1-naphthyl ethylamine hydrochloride and cinacalcet hydrochloride are easily separated by simple operation of extraction, and the purity of (R)-1-naphthyl ethylamine obtained by extraction is sufficient to be recycled for preparation of next batch cinacalcet hydrochloride after adjusting pH.

The present invention is easy to operate and convenient in the post treatment, the resulted yield is high, the (R)-1-naphthyl ethylamine is easily recycled, and cinacalcet hydrochloride obtained is of good quality with low content of related substance. The present invention is suitable to be used in industrialized production with great application value.

DETAILED DESCRIPTION OF THE INVENTION

The following examples further describe the present invention in details but do not limit the scope of the present invention. One of ordinary skill in the art knows how to make modifications based on the examples without departing from the scope of the present invention.

Example 1

3-(3-(trifluoromethyl)phenyl)propyl methanesulfonate (4 g), toluene (57 mL), R-(−)-1-naphthyl ethylamine (2.91 g) and potassium carbonate (1.96 g) were added into the reactor, the mixture was refluxed for 7 hours, The mixture was cooled to 20° C.-25° C., water (100 mL) and toluene (10 mL) were added. The organic phase was separated, and washed with HCl (1 M, 20 mL×3) at 50° C., then organic phase was stirred at 5° C.-10° C. for one hour. filter and obtain 4.58 g cinacalcet hydrochloride, the yield is 82%. The aqueous layer was combined, adjusted to pH=14 with NaOH (10%) and extracted with toluene (30 mL). The organic phase was dried over anhydrous sodium sulfate, filtered and concentrated to afford recovered R-(−)-1-naphthyl ethylamine, 0.33 g.

Cinacalcet hydroxide obtained in this implement is confirmed by tests:

HPLC purity (purity): 99.0%; Chiral purity (purity): 99.0%; MS (ESI): m/z=358 [M+H$^+$]; $^1$HNMR (400 MHz, CDCl$_3$): δ=1.97-1.99 (d, 3H), 2.21-2.32 (m, 2H), 2.46-2.57 (m, 2H), 2.72-2.79 (m, 2H), 5.17-5.21 (t, 1H), 7.16-7.27 (m, 3H), 7.33-7.31 (d, J=7.2 Hz, 2H), 7.54-7.65 (m, 3H), 7.88-7.98 (m, 3H), 8.23-8.25 (d, J=7.2 Hz, 1H), 10.07-10.09 (d, J=7.2 Hz, 1H), 10.61 (s, 1H); $^{13}$C NMR (400 MHz, CDCl$_3$): δ=21.32 (CH$_3$), 27.30 (CH$_2$), 32.51 (CH$_2$), 45.49 (CH$_2$), 53.53 (CH), 121.26, 122.62, 123.09, 124.88, 125.03, 125.33 (CF$_3$), 126.13, 126.27, 127.35, 128.04, 128.85, 129.51, 129.56, 130.19, 130.69, 131.55, 132.10, 133.87, 140.78. The structure of R-(−)-1-naphthyl ethylamine as recovered is confirmed by the test result of MS (ESI): m/z=172[M+H+].

Example 2

R-(−)-1-naphthyl ethylamine (0.33 g recovered from example 1, +2.58 g), toluene (57 mL), 3-(3-(trifluoromethyl) phenyl)propyl methanesulfonate (4.0 g), and potassium carbonate (1.96 g) were charged and refluxed for 10 hours. The mixture was cooled to 20° C.-25° C., water (20 mL) and toluene (20 ml) were added. Organic phase was separated and washed with hydrochloric acid (1 mol/L, 20 mL×3) at 50° C., chilled and stirred at 0° C.-5° C. for one hour. Solid was collected by filtration to afford cinacalcet hydrochloride at 4.50 g, and confirmed as Example 1 to have HPLC purity (Purity) at 99.2% and Chiral purity (Purity) at 99.0%.

Example 3

R-(−)-1-naphthyl ethylamine (4 g), toluene (65 mL), 3-(3-(trifluoromethyl)phenyl) propyl methanesulfonate (4.86 g), and potassium carbonate (1.96 g) were charged and refluxed for 16 hours. The mixture was cooled to 20° C.-30° C., water (150 mL) and toluene (10 ml) were added. Organic phase was separated and washed with hydrochloric acid (2 mol/L, 20 mL×3) at 60° C., chilled and stirred at 10° C.-15° C. for one hour. Solid was collected by filtration to afford cinacalcet hydrochloride, 4.4 g, 79%, and confirmed that HPLC purity (Purity) is 99.0% and Chiral purity (Purity) is 99.0%.

The aqueous layer was combined, adjusted to pH=13 with NaOH (10%) and extracted with acetonitrile (12 ml×3). The organic phase was dried over anhydrous sodium sulfate, filtered and concentrated to afford recovered R-(−)-1-naphthyl ethylamine, 2.0 g. The results were confirmed as in Example 1 MS (ESI): m/z=172[M+H+].

Example 4

3-(3-(trifluoromethyl)phenyl)propyl methanesulfonate (5.1 g), dimethylbenzene (32 ml), R-(−)-1-naphthyl ethylamine (2.91 g), and potassium hydroxide (0.80 g) were charged and refluxed for 5 hours, the mixture was cooled to 20° C.-30° C., water (20 ml) and dimethylbenzene (32 ml) were added, organic phase was separated and washed with hydrochloric acid (2 mol/L, 10 mL×3) at 40° C., chilled and stirred at 0° C.-5° C. for one hour. Solid was collected by filtration to afford cinacalcet hydrochloride, 4.24 g, 76%. Cinacalcet hydroxide obtained in this example was tested and confirmed with the same method as used in example 1:

HPLC purity (Purity): 98.5%; Chiral purity (Purity): 99.0%.

The aqueous layer was combined, adjusted to pH=12 with NaOH (10%) and extracted with acetonitrile (20 ml×4). The organic phase was dried over anhydrous sodium sulfate, filtered and concentrated to afford recovered R-(−)-1-naphthyl ethylamine, 3.8 g. The R-(−)-1-naphthyl ethylamine recovered in this example was tested and confirmed with the same method as used in Example 1.

Example 5

3-(3-(trifluoromethyl)phenyl)propyl trifluoromethanesulfonate (4.8 g), toluene (16 ml), R-(−)-1-naphthyl ethylamine (2.91 g), and potassium hydroxide (1.14 g), was charged and refluxed for 6 hours, The mixture was cooled to 20° C.-25° C., water (20 ml) and toluene (20 ml) were added, Organic phase was separated and washed with hydrochloric acid (1 mol/L, 20 mL×3) at 50° C., chilled and stirred at 20° C.-25° C. for 1 hour. Solid was collected by filtration to afford cinacalcet hydrochloride, 4.4 g, 79%. Cinacalcet hydrochloride obtained in this example was tested and confirmed with the same method as used in example 1: HPLC purity (Purity): 99.0%; Chiral purity (Purity): 99.0%.

The aqueous layer was combined, adjusted to pH=14 with NaOH (10%) and extracted with toluene (30 ml×4). The organic phase was dried over anhydrous sodium sulfate, filtered and concentrated to afford recovered R-(−)-1-naphthyl ethylamine, 0.34 g. The R-(−)-1-naphthyl ethylamine recovered in this example was tested and confirmed with the same method as used in Example 1.

Example 6

3-(3-(trifluoromethyl)phenyl)propyl trifluoromethanesulfonate (4.0 g), toluene (50 ml), R-(−)-1-naphthyl ethylamine (7.28 g), and potassium hydroxide (1.96 g), was charged and refluxed for 16 hours, the mixture was cooled to 20° C.-25° C., water (50 ml) and toluene (50 ml) were added, organic phase was separated and washed with hydrochloric acid (3 mol/L, 20 mL×3) at 80° C., chilled and stirred at 0° C.-5° C. for 1 hour. Solid was collected by filtration to afford cinacalcet hydrochloride, 4.9 g, 89%. Cinacalcet hydrochloride obtained in this example was tested and confirmed with the same method as used in Example 1: HPLC purity (Purity): 99.0%; Chiral purity (Purity): 99.0%.

The aqueous layer was combined, adjusted to pH=13 with NaOH (10%) and extracted with ethyl acetate (15 ml×5 mL). The organic phase was dried over anhydrous sodium sulfate, filtered and concentrated to afford recovered R-(−)-1-naphthyl ethylamine, 4.4 g. The R-(−)-1-naphthyl ethylamine recovered in this example was tested and confirmed with the same method as used in Example 1.

Example 7

3-(3-(trifluoromethyl)phenyl)propyl methanesulfonate (4 g), toluene (32 ml), R-(−)-1-naphthyl ethylamine (4.86 g), and potassium carbonate (3 g) was charged and refluxed for 16 hours, the mixture was cool to 20° C.-25° C., water (30 ml) and toluene (30 ml) were added, Organic phase was separated and washed with hydrochloric acid (1 mol/L, 50 mL×3) at 70° C., chilled and stirred at 0° C.-5° C. for 1 hour. Solid was collected by filtration to afford cinacalcet hydrochloride, 4.7 g, 85%.

Cinacalcet hydroxide obtained in this example is tested and confirmed with the same method as used in example 1: HPLC purity (Purity): 99.0%; Chiral purity (Purity): 99.0%.

The aqueous layer was combined, adjusted to pH=14 with NaOH (10%) and extracted with toluene (15 mL×2). The organic phase was dried over anhydrous sodium sulfate, filtered and concentrated to afford recovered R-(−)-1-naphthyl ethylamine, 2.1 g.

The R-(−)-1-naphthyl ethylamine recovered in this example was tested and confirmed with the same method as used in Example 1.

Example 8

1-(3-bromopropyl)-3-(trifluoromethyl)benzene (3.8 g), toluene (30 ml), R-(−)-1-naphthyl ethylamine (2.91 g), and potassium carbonate (3.92 g) was charged and refluxed for 7 hours, The mixture was cooled to 20° C.-25° C., water (100 ml) and toluene (30 ml) were added, organic phase was separated and washed with hydrochloric acid (1 mol/L, 40 mL×3) at 50° C., chilled and stirred at 5° C.-10° C. for 1 hour. Solid was collected by filtration to afford cinacalcet hydrochloride, 4.6 g, 83%. Cinacalcet hydroxide obtained in this example was tested and confirmed with the same method as used in Example 1: HPLC purity (Purity): 98.7%; Chiral purity (Purity): 99.0%.

The aqueous layer was combined, adjusted to pH=13 with NaOH (10%) and extracted with toluene (15 mL×3). The organic phase was dried over anhydrous sodium sulfate, filtered and concentrated to afford recovered R-(−)-1-naphthyl ethylamine 0.33 g.

The R-(−)-1-naphthyl ethylamine recovered in this example was tested and confirmed with the same method as used in Example 1.

Example 9

1-(3-chloropropyl)-3-(trifluoromethyl)benzene (3.15 g), toluene (50 ml), R-(−)-1-naphthyl ethylamine (2.91 g), and potassium carbonate (1.96 g) was charged and refluxed for 15 hours, the mixture was cooled to 15° C.-20° C., water (50 ml) and toluene (50 ml) were added, organic phase was separated and washed with hydrochloric acid (2 mol/L, 10 mL×3) at 60° C., chilled and stirred at 5° C.-10° C. for 1 hour. Solid was collected by filtration to afford cinacalcet hydrochloride, 4 g, 73%. Cinacalcet hydroxide obtained in this example was tested and confirmed with the same method as used in Example 1: HPLC purity (Purity): 97.0%; Chiral purity (Purity): 98.0%.

The aqueous layer was combined, adjusted to pH=12 with NaOH (10%) and extracted with toluene (20 mL×1). The organic phase was dried over anhydrous sodium sulfate, filtered and concentrated to afford recovered R-(−)-1-naphthyl ethylamine 0.3 g.

The R-(−)-1-naphthyl ethylamine recovered in this example was tested and confirmed with the same method as used in Example 1.

Example 10

3-(3-(trifluoromethyl)phenyl)propyl methanesulfonate (4.0 g), toluene (50 ml), R-(−)-1-naphthyl ethylamine (2.42 g), and sodium bicarbonate (1.53 g) was charged and refluxed for 16 hours, the mixture was cooled to 20° C.-25° C., water (50 ml) and toluene (50 ml) were added, organic phase was separated and washed with hydrochloric acid (2 mol/L, 10 mL×3) at 80° C., chilled and stirred at 0° C.-5° C. for 1 hour. Solid was collected by filtration to afford cinacalcet hydrochloride, 4.1 g, 73%.

Cinacalcet hydroxide obtained in this example was tested and confirmed with the same method as used in Example 1: HPLC purity (Purity): 99.0%; Chiral purity (Purity): 99.0%.

The aqueous layer was combined, adjusted to pH=14 with NaOH (10%) and extracted with toluene (20 mL×1). the organic layer was dried with anhydrous sodium sulfate, distill and remove toluene, basically no R-(−)-1-naphthyl ethylamine was recovered.

Example 11

3-(3-(trifluoromethyl)phenyl)propyl methanesulfonate (4.0 g), toluene (50 ml), of R-(−)-1-naphthyl ethylamine (2.0 g), and sodium carbonate (3.0 g), was charged and refluxed for 16 hours, The mixture was cooled to 5° C.-10° C., water (50 ml) and toluene (50 ml) were added, Organic phase was separated. Extract water phase with toluene 30 mL×3, combine the organic phases and dry with anhydrous sodium sulfate, filter and distill the solvent, then cinacalcet is obtained. Add 30 ml of 2 mol/L hydrochloric acid, stir to formulahydrochloride, distill the solvent, afford cinacalcet hydrochloride, 3.0 g, 55%.

Cinacalcet hydroxide obtained in this example was tested and confirmed with the same method as used in Example 1: HPLC purity (Purity): 88.0%; Chiral purity (Purity): 99.0%.

The result of the example shows that the contents of dialkylation compound (Formula IV Compound) and carbamate impurity (Formula III Compound) in the product are respectively 10.0% and 1.5%, the cause is that the excessive amount of Formula II Compound will result in the large amount of dialkylation impurity (Formula IV Compound) existing in end product of alkylation reaction, which is hard to be separated from cinacalcet because it's an alkaline substance. In another aspect, excessive Formula II Compound results in the formation of large amount of carbamate impurity (Formula III Compound), finally increase the hardship of separation and purification in the post treatment, the yield decreases.

We claim:
1. A process for preparing cinacalcet hydrochloride, comprising
   charging (R)-1-naphthyl ethylamine (Formula I) and 3-(trifluoromethyl) benzene compound (Formula II)

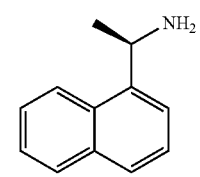

Formula I

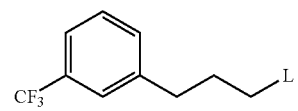

Formula II at a molar ratio of 1.0:1 to 5.0:1 in a suitable organic solvent,
   heating and refluxing until the 3-(trifluoromethyl) benzene compound is completely consumed in presence of an inorganic base,
   obtaining a mixture containing cinacalcet,
   obtaining cinacalcet hydrochloride having a formula of

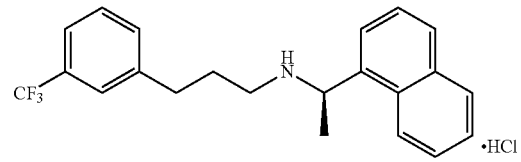 [SMILES: C[C@@H](NCCCc1cccc(C(F)(F)F)c1)c1cccc2ccccc12 ; Cl]

from the mixture containing cinacalcet after acidification with hydrochloride and extraction,
   washing the mixture containing cinacalcet with water to obtain an aqueous layer and an organic layer, separating and removing the aqueous layer, and adding hydrochloric acid to the organic layer to obtain a mixture of the organic layer and the hydrochloric acid layer,
   heating the mixture of the organic layer and the hydrochloric acid layer to about 40-80° C. until a two-phase system is clear, and separating the two-phase system into the separated organic layer and the separated hydrochloric acid layer,
   allowing the separated organic layer to cool down to about 0° C.-30° C., and obtaining cinacalcet hydrochloride by crystallizing and filtering, and
   adjusting pH of the separated hydrochloric acid layer with a second inorganic base to 8 to 14, extracting the separated hydrochloric acid layer with a second organic solvent at 1 to 10 times w/v of the (R)-1-naphthyl ethylamine charged for 1-5 times, combining organic layers from the extraction, and concentrating the combined organic layer to recover the (R)-1-naphthyl ethylamine of formula I,
wherein L in Formula II is a halogen, methanesulfonate, p-toluenesulfonate, or triflate.

2. The process as described in claim 1, wherein the molar ratio of the (R)-1-naphthyl ethylamine to the 3-(trifluoromethyl) benzene compound is in a range of 1.0:1 to 3.0:1.

3. The process as described in claim 2, wherein the molar ratio of the (R)-1-naphthyl ethylamine to the 3-(trifluoromethyl) benzene compound is in a range of 1.0:1 to 2.0:1.

4. The process as described in claim 1, wherein the molar ratio of the inorganic base to the (R)-1-naphthyl ethylamine is in a range of 1.0:1 to 2.0:1.

5. The process as described in claim 1, wherein the inorganic base is $K_2CO3$, $Na_2CO_3$, $KHCO_3$, $NaHCO_3$, KOH, or NaOH.

6. The process as described in claim 1, wherein the organic solvent is toluene, xylene, actonitrile, or a mixture thereof.

7. The process as described in claim 6, wherein the organic solvent is toluene or xylene.

8. The process as described in claim 1, wherein the hydrochloric acid is added to the organic layer at a molar ratio of the hydrochloric acid to the (R)-1-naphthyl ethylamine charged of 1.0:1 to 5.0:1.

9. The process as described in claim 1, wherein the second inorganic base is $K_2CO_3$, $Na_2CO_3$, $KHCO_3$, $NaHCO_3$, KOH, or NaOH.

10. The process as described in claim 1, wherein the second organic solvent is toluene, ethyl acetate, dichloromethane, methyl tert-butyl ether, methyl tert-butyl ketone, or acetonitrile.

11. The process as described in claim 1, wherein the second organic solvent is toluene, ethyl acetate, acetonitrile, or dichloromethane.

* * * * *